Figure 1:
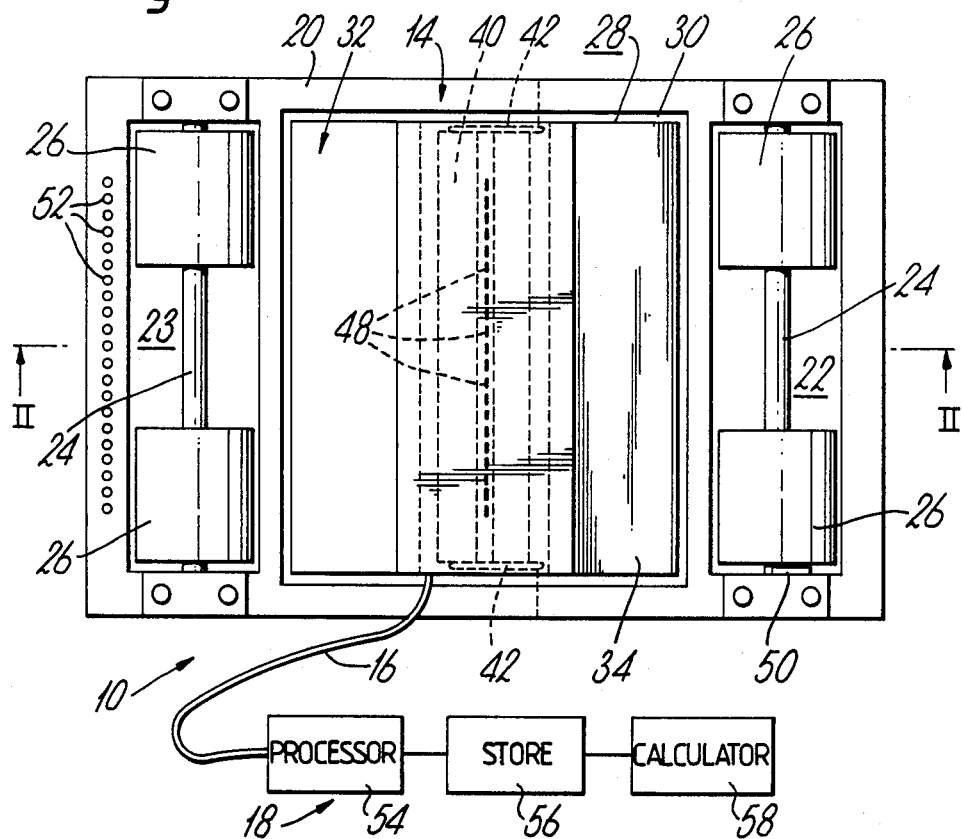

United States Patent [19]

Saunderson

[11] Patent Number: 4,814,705

[45] Date of Patent: Mar. 21, 1989

[54] METHOD AND APPARATUS FOR MAGNETIC DISCONTINUITY DETECTION IN A SPECIMEN OF MAGNETIZABLE MATERIAL

[75] Inventor: David H. Saunderson, Wantage, England

[73] Assignee: The Secretary of State for United Kingdom Atomic Energy Authority in Her Britannic Majesty's Government of the United Kingdom of Great Britain and Northern Ireland, London, England

[21] Appl. No.: 16,576

[22] Filed: Feb. 19, 1987

[30] Foreign Application Priority Data

Mar. 17, 1986 [GB] United Kingdom ............... 8606564

[51] Int. Cl.⁴ .................. G01N 27/83; G01R 33/06
[52] U.S. Cl. .................... 324/225; 324/235; 324/238; 324/262; 364/571.01
[58] Field of Search ............ 324/200, 202, 217–221, 324/225–227, 232–235, 238–243, 262; 364/571, 575, 581, 582, 571.01, 571.02, 571.05

[56] References Cited

U.S. PATENT DOCUMENTS

| | | | |
|---|---|---|---|
| 2,549,916 | 4/1951 | Mesh . | |
| 3,015,063 | 12/1961 | Ownby | 324/221 |
| 3,284,701 | 11/1966 | Kerbow | 324/221 X |
| 3,484,682 | 12/1969 | Wood | 324/227 |
| 3,609,530 | 9/1971 | Joinson | 324/225 X |
| 3,745,452 | 7/1973 | Osburn et al. | 324/254 |
| 4,087,749 | 5/1978 | McCormack | 324/225 |
| 4,523,148 | 6/1985 | Maciejewski | 324/351 |
| 4,573,013 | 2/1986 | Kusenberger et al. | 324/238 |
| 4,634,976 | 1/1987 | Tiitto | 324/262 X |
| 4,648,041 | 3/1987 | Tarr | 324/227 |

FOREIGN PATENT DOCUMENTS

| | | |
|---|---|---|
| 0021893 | 1/1981 | European Pat. Off. . |
| 0092094 | 10/1983 | European Pat. Off. . |
| 1169752 | 11/1969 | United Kingdom . |
| 2159954A | 12/1985 | United Kingdom . |

Primary Examiner—Gerard R. Strecker
Attorney, Agent, or Firm—William R. Hinds

[57] ABSTRACT

A method and an apparatus are provided for detecting magnetic discontinuities, for example corrosion pits, in a specimen of magnetizable material. A horseshoe shaped magnet (32) is supported with its poles just clear of a surface of the specimen (12) by a wheeled frame (20), and is moved over the surface. An array of sensors (48) between the poles detects the leakage flux near the surface. The signal from any one sensor at a particular location is corrected by subtracting from it the average of the signals from the same sensor at a plurality of other locations preceding and following that location. If the corrected signal exceeds a threshold value, this indicates abnormally large localized leakage flux, and so indicates metal loss from the specimen.

9 Claims, 1 Drawing Sheet

U.S. Patent　　Mar. 21, 1989　　4,814,705

METHOD AND APPARATUS FOR MAGNETIC DISCONTINUITY DETECTION IN A SPECIMEN OF MAGNETIZABLE MATERIAL

This invention relates to a method and an apparatus for detecting magnetic discontinuities in a specimen of a magnetisable material.

It is known, for example from UK Patent No. GB 1 261 346, that discontinuities such as cracks in a specimen of magnetisable material can be detected by magnetising the material and sensing variations in the leakage flux near the surface of the specimen which are due to the discontinuity. The magnetisation may be produced by a permanent magnet, possibly of horseshoe shape; and the leakage flux can be sensed with a Hall effect device. A problem faced by such a detector is that the magnitude of the leakage flux depends upon the magnetisation of the adjacent portion of the material, and so varies with the effective gap between the magnet poles and the surface of the specimen, and also varies with proximity to edges of the specimen.

According to the present invention there is provided a method of detecting magnetic discontinuities in a specimen of a magnetisable material comprising inducing a magnetic field within the specimen, arranging a linear array of equally spaced sensors to detect leakage flux near the surface of the specimen and to provide an electrical signal representing the leakage flux, moving the array of sensors over the surface, recording values of the signals representing the leakage flux at successive, equally spaced locations of each sensors, and subsequently for each said location of each sensor calculating the difference between the recorded value at the location and a baseline equal to a weighted average of those recorded values corresponding to a predetermined plurality of locations in the vicinity of the said location.

Correcting the signals representing leakage flux by means of this varying baseline overcomes the above-mentioned problem.

In calculating the baseline, the predetermined plurality of locations includes locations preceding the said location and locations following the said location, for example the average might be taken of the recorded values of the ten preceding and ten following locations.

Each sensor might be arranged to detect the leakage flux perpendicular to the surface; or the leakage flux tangential to the surface and either parallel, or perpendicular, to the direction of movement of the sensor. Indeed it may be arranged to detect any combination of these three components of the leakage flux. However movement of the means for inducing the magnetic field creates eddy currents whose magnetic flux depends upon the speed of the movement, and preferably the leakage flux is detected tangential to the surface to minimize the effect of such eddy currents.

In the method of the invention the array of sensors is moved over the surface in a direction transverse to the orientation of the array. Surprisingly the spacing between adjacent sensors in such a linear array can be three or four times greater than the distance between successive locations of any one sensor at which the signal is recorded along the direction of movement. Consequently in the method of the invention the distance between successive said locations is above a quarter of the distance between adjacent sensors in the array. The signals from the sensors are preferably multiplexed. In calculating the baseline, the plurality of locations from which the recorded values are taken may all be locations of one sensor, or may include locations of other sensors.

The invention also provides an apparatus which operates in the manner defined above for detecting magnetic discontinuities in a specimen of a magnetisable material.

The magnetic field is induced by means which preferably comprise a horseshoe shaped magnet (either a permanent magnet or an electromagnet) with poles spaced apart, supported just clear of the surface so as to be free to move, for example by wheels. The sensors might be Hall effect devices or magneto-resistors, and are preferably located between the magnet poles.

Where the sensors are Hall effect devices they are prferably mounted on a heat sink bar which may be thermostatically held at above ambient temperature so as to minimize temperature variations in operation. Furthermore it may be necessary to process the signal from each sensor, so as to obtain the desired signal representing the magnetic leakage flux, for example by correcting for any zero-offset, or to take into consideration differences in sensitivity between different sensors in the array.

The apparatus incorporating a linear array of sensors enables corrosion to be detected on either surface of a plate-shaped specimen; and enables a large area of the specimen to be tested for localised corrosion comparatively rapidly.

Figure 2:
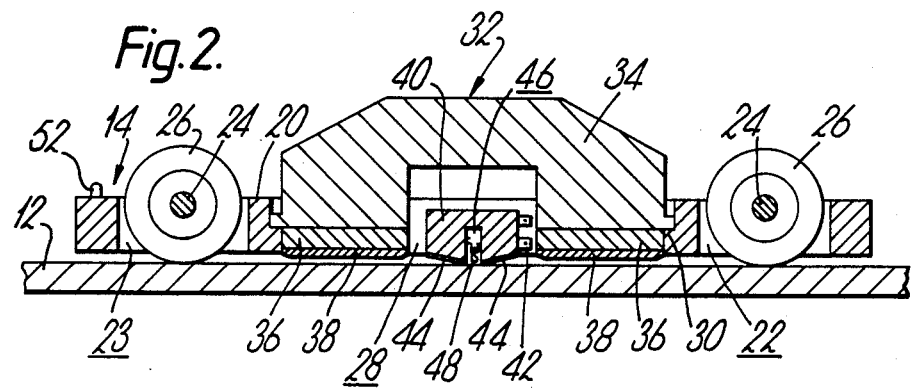

The invention will now be further described, by way of example only, and with reference to the accompanying drawings, in which:

FIG. 1 shows a plan view, partly diagrammatic, of an apparatus for detecting magnetic discontinuities; and FIG. 2 shows a sectional view on the line II—II of FIG. 1.

Referring to FIGS. 1 and 2, an apparatus 10 for detecting magnetic discontinuities, and in particular corrosion pits in a steel plate 12, consists of a trolley 14 connected by a long flexible electrical cord 16 to electronic circuitry 18 (shown diagrammatically in FIG. 1). The trolley 14 comprises an open rectangular frame 20 of non-magnetic material, defining front and rear rectangular spaces 22, 23 in which are mounted respective axles 24 each with two rollers or wheels 26, and a central rectangular space 28 with a narrow internal flange 30 to support a magnet 32 of a generally horseshoe shaped cross-section. The magent 32 consists of a mild steel yoke 34 supported around its lower edges by the flange 30, each lower face of the yoke 34 carrying a flat rectangular permanent magnet 36 of rare-earth cobalt alloy with a mild steel pole piece 38 on its lower face. The two permanent magnets 36 are arranged so that the two pole pieces 38 are of opposite polarity. The pole pieces 38 are close to the upper surface of the plate 12, and so a magnetic field is induced in that portion of the plate 12 between the pole pieces 38.

In the gap between the pole pieces 38 is a nylon block 40, connected to the sides of the frame 20 by trailing parallel arm linkages 42 so as to be free to ride up and down over any undulations in the surface of the plate 12 while maintaining its orientation. The block 40 has chamfered lower faces covered by molybdenum shims 44 to minimise friction and wear. There is a wide slot 46 along the lower face of the block 40 in which is fixed a printed circuit board (not shown) carrying a linear array of twenty-one Hall effect sensors 48, the separation between adjacent sensors 48 being 12.5 mm. An aluminium bar (not shown) extends along the circuit board in thermal contact with each sensor 48, and an electrical heater (not shown) and temperature sensor (not shown) enable the bar and hence the sensors 48 to be held at a steady temperature slightly above ambient. The sensors 48 are oriented and arranged so as to detect any leakage flux near to and tangential to the surface and parallel to the direction of motion of the trolley 14.

An encoder 50 is arranged to detect rotation of one of the front rollers 26, signals from the encoder 50 being supplied to a multiplexer (not shown) on the printed circuit board, to which signals from all the sensors 48 are supplied. In operation the trolley 14 is moved steadily over the surface of the plate 12 either manually (by an operator) or by an electric motor (not shown) and the multiplexer is controlled by the signals from the encoder 50 so as to output along the electrical cord 16 the signals from each sensor 48 in turn, at such a rate that a signal is output from each sensor 48 for every 3 mm forward motion of the trolley 14. Along the rear edge of the frame 20 is a linear array of twenty one indicator lamps 52, each aligned with a respective sensor 48.

Referring to FIG. 1 the electronic circuitry 18 consists of a signal processor 54, a signal store 56, and a calculator 58. When the signal from a sensor 48 is to be read by the multiplexer, an appropriate correction voltage for the zero-offset as previously determined for that sensor 48 is supplied by the processor 54 through the electrical cord 16 and the multiplexer, so as to correct for the zero-offset; the resulting signal is then digitised and transmitted by the multiplexer to the processor 54. The processor 54 then applies an appropriate amplification to account for the previously determined sensitivity of that sensor 48. Consequently the signals output by the processor 54 accurately represent the flux to which the corresponding sensors 48 are exposed, and if all the sensors 48 are exposed to the same flux then all the signals output by the processor 54 will be equal. The signals output from the processor 54 are recorded in the store 56.

Each signal recorded in the store 56 is then corrected by the calculator 58, by subtracting from it a baseline equal to the average of the ten previous and the ten subsequent recorded signals corresponding to the same sensor 48. If the resulting corrected signal differs from zero by more than a preset threshold this is taken as an indication that there was an unacceptable degree of leakage flux at the corresponding location on the plate 12. As the rear edge of the trolley 14 passes over that location the indicator light 52 aligned with the corresponding sensor 48 is caused to light up, so that an operator has a visual indication of the locations at which there was excess leakage flux, such an excess leakage flux being indicative of a hole through the plate 12 or of a corrosion pit in the plate 12, or other metal loss. In addition to the lighting up of the indicator lamp 52, a further visual indication may be given by simultaneously and briefly stopping the electric motor, where such a motor is provided.

It will be understood that the signals output from the processor 54 might also be stored on magnetic disks or tape, for subsequent correction; and/or that the corrected signals determined by the calculator 58 might be supplied to a graph plotter (not shown) to produce a printed plan indicating the locations of such excess leakage flux on the plate 12.

The apparatus 10 has been found able to detect corrosion pits on either surface of the plate 12, down to as small as a 3 mm deep, 120° conical pit in a 6 mm thick plate. The perturbation in the leakage flux due to a pit gives an indication of the volume of the pit, but not of its shape unless the pit is more than about 20 mm broad. A circular pit is found to perturb the leakage flux over an oval area of the plate, the narrowest dimension of the oval being parallel to the direction of the applied magnetic field and being only slightly larger than the pit's diameter, while the widest dimension of the oval is perpendicular to the direction of the applied magnetic field and is four or five times the pit's diameter. Although the apparatus 10 has been shown as resting directly on the surface of the steel plate 12, it will operate equally effectively where it is separated from the steel plate by a thin layer of non-magnetic material, for example a layer of concrete, so that it can be used to detect corrosion pits in steel girders embedded in concrete provided the concrete layer is not more than a few centimetres thick.

It will be appreciated that the number of previous and subsequent recorded signals over which the average is taken to calculate the baseline might be different from that stated above, and that multiplexer might be arranged to scan the signals from the sensors 48 more frequently or less frequently than as stated above. It will also be appreciated that in determining the baseline, use might also be made of recorded signals from other sensors in the array, for example the average might be taken of recorded signals corresponding to locations in a rectangular area of the surface, or in circular area of the surface, surrounding the location corresponding to the signal from which the baseline is to be subtracted; and furthermore, different weights might be given to recorded signals from different locations, for example in inverse proportion to their distance from the said location. It will be further appreciated that, if desired, slots might be provided in the pole pieces 38 to locate magnetic sensors, so that variations in the inducing magnetic field due to variations in lift-off can be taken into account. Movement of the block 40 and hence the array of sensors 48 up and down, due to surface undulations, tends to affect the signals from all the sensors 48 equally, and so may be compensated for by subtracting the average of the corrected signals from all the other sensors 48 in the array from the corrected signal corresponding to a specific location.

The apparatus 10 described above is designed for testing flat plates 12; where it is desired to test curved plates or pipes similar apparatus could be used but with curved pole pieces and a curved linear array of sensors to fit the curvature of the surface. Where a thin rod is to be tested only one sensor is required, and so the multiplexer can be dispensed with.

I claim:

1. A method of detecting magnetic discontinuities in a specimen of a magnetisable material comprising:
    (a) including a magnetic field within the specimen,
    (b) arranging a linear array of equally spaced sensors to detect magnetic leakage flux near the surface of the specimen due to said magnetic field within the specimen and to provide electrical signals representing the leakage flux,
    (c) moving the array of sensors over the surface in a direction transverse to the orientation of the array, (d) recording values of the signals representing the leakage flux at successive, equally spaced locations of each sensor, the distance between successive said locations being about a quarter of the distance between adjacent sensors in the array, and (e) subsequently for each said location of each sensor calculating a baseline, the baseline being equal to a weighted average of those recorded values corresponding to a predetermined plurality of locations in the vicinity of the said location, the said plurality of locations including locations preceding the said location and locations following the said location, (f) and then for each said location of each sensor calculating the difference between the recorded value at that location and the corresponding baseline, the difference so calculated being indicative of any magnetic discontinuity.

2. A method as claimed in claim 1 wherein the plurality of locations from which the baseline is determined are a predetermined number of locations of the said sensor preceding the said location and the same number of locations of the said sensor following the said location.

3. A method as claimed in claim 1 wherein the plurality of locations from which the baseline is determined includes locations of other sensors of the array in the vicinity of the said location of the said sensor.

4. A method as claimed in claim 1 wherein the baseline is the average of the recorded values corresponding to the predetermined plurality of locations, all these recorded values being weighted equally.

5. An apparatus for detecting magnetic discontinuities in a specimen of a magnetisable material comprising:

(a) a trolley movable over a surface of the specimen, (b) means supported by the trolley for inducing a magnetic field within the specimen, (c) means supported by the trolley forming a linear array of equally spaced sensors for detecting magnetic leakage flux near the surface of the specimen due to the said magnetic field within the specimen and for providing electrical signals representing the leakage flux, the array of sensors being movable over the surface transverse to the orientation of the array, (d) means for measuring the distance the trolley and hence the array moves over the surface, (e) means responsive to the distance measuring means for recording values of the signals representing the leakage flux at successive equally spaced locations of each sensor during movement of the array over the surface, the distance between successive said locations being about a quarter of the distance between adjacent sensors in the array, and (f) means for calculating, for each said location of each sensor, a baseline, the baseline being equal to a weighted average of those recorded values corresponding to a predetermined plurality of locations in the vicinity of the said location, the said plurality of locations including locations preceding the said location and locations following the said location, and then for each said location of each sensor calculating the difference between the recorded value at that location and the corresponding baseline, this difference being indicative of any magnetic discontinuity.

6. An apparatus as claimed in claim 5 wherein the inducing means comprises a horseshoe shaped magnet with two poles of opposite polarity spaced apart and supported just clear of the surface so as to be movable over the surface.

7. An apparatus as claimed in claim 5 wherein the array of sensors is mounted onto a heat sink member, and means are provided to maintain the member at a substantially constant temperature above ambient temperature during operation.

8. An apparatus as claimed in claim 5 wherein the array of sensors is connected to the inducing means by a parallel arm linkage so as to be free to ride up and down over any undulations of the surface while maintaining its orientation relative to the surface.

9. An apparatus as claimed in claim 5 also including means for indicating any location for which the said difference exceeds a preset threshold value.

* * * * *

UNITED STATES PATENT AND TRADEMARK OFFICE
CERTIFICATE OF CORRECTION

PATENT NO. : 4,814,705
DATED : March 21, 1989
INVENTOR(S) : SAUNDERSON, DAVID H.

It is certified that error appears in the above—identified patent and that said Letters Patent is hereby corrected as shown below:

On the first page of the patent, the information page, the information relating to the assignee is changed as follows:

--[73] Assignee: United Kingdom Atomic Energy Authority, London, England--

Signed and Sealed this

Second Day of January, 1990

*Attest:*

JEFFREY M. SAMUELS

*Attesting Officer*     *Acting Commissioner of Patents and Trademarks*